United States Patent [19]

Clokie

[11] Patent Number: 5,702,695

[45] Date of Patent: Dec. 30, 1997

[54] OSSEOINTEGRATION PROMOTING IMPLANT COMPOSITION, IMPLANT ASSEMBLY AND METHOD THEREFOR

[75] Inventor: Cameron Malcolm Lang Clokie, Westmount, Canada

[73] Assignee: McGill University, Canada

[21] Appl. No.: 481,501

[22] PCT Filed: Nov. 14, 1994

[86] PCT No.: PCT/CA94/00626

§ 371 Date: Jun. 16, 1995

§ 102(e) Date: Jun. 16, 1995

[87] PCT Pub. No.: WO95/13099

PCT Pub. Date: May 18, 1995

[51] Int. Cl.⁶ .................. A61K 31/765; A61C 13/00
[52] U.S. Cl. .................. 424/78.08; 424/78.37; 424/78.38; 424/423; 433/201.1; 514/12; 514/13
[58] Field of Search .................. 424/422, 423, 424/78.08

[56] References Cited

U.S. PATENT DOCUMENTS

| | | | |
|---|---|---|---|
| 5,158,934 | 10/1992 | Ammann et al. | 514/12 |
| 5,264,214 | 11/1993 | Rhee et al. | 424/422 |
| 5,270,300 | 12/1993 | Hunziker | 514/12 |
| 5,409,896 | 4/1995 | Ammann et al. | 514/13 |
| 5,422,340 | 6/1995 | Ammann et al. | 514/12 |
| 5,447,966 | 9/1995 | Hermes | 523/113 |

FOREIGN PATENT DOCUMENTS

| | | |
|---|---|---|
| 0321277 | 6/1989 | European Pat. Off. . |
| 0361896 | 4/1993 | European Pat. Off. . |
| 90 04974 | 5/1990 | WIPO . |

*Primary Examiner*—Peter F. Kulkosky
*Attorney, Agent, or Firm*—Bachman & LaPointe, P.C.

[57] ABSTRACT

A liquid composition comprising a transforming growth factor β(TGF-/β in a polyoxyalkylene block copolymer—containing liquid carrier which gels at about 37 C, promotes osseointegration of an implant in bone, when introduced into a bore in the bone, prior to the insertion of the implant in the bone.

11 Claims, 2 Drawing Sheets

OSSEOINTEGRATION PROMOTING IMPLANT COMPOSITION, IMPLANT ASSEMBLY AND METHOD THEREFOR

TECHNICAL FIELD

This invention relates to a method of placing an implant in bone, to an osseointegration promoting implant composition, use of the composition, use of transforming growth factor β in the manufacture of such a composition and to an implant assembly.

BACKGROUND ART

Metal implants have revolutionized the field of prosthetic dentistry and orthopaedics. The basic principle of implants is that screws, usually of titanium, are surgically inserted into human bones providing a foundation upon which a prosthetic device can be built. A metal implant system widely employed in prosthetic dentistry is the Branemark System, which is based on a discovery of Dr. Per-Ingvar Branemark.

A major disadvantage with present dental implant therapy, such as that of the Branemark System, is patient discomfort caused by two lengthy surgical procedures, with lengthy intervals being required between these procedures and final dental prosthesis insertion.

In the existing procedure a screw-like implant element is first inserted in a surgically formed bore in the bone and is then left for a period of about three to six months to permit the implant element to integrate or weld with the bone; the implant element has an internal threaded bore for subsequent threaded mounting of a support base or abutment for a prosthetic device. A temporary cover is applied over the exposed end of the implant element, so that the implant element is unloaded within the bone, beneath the gingival tissues.

When the implant element is adequately integrated or welded in the bore of the bone, the temporary cover is removed and the support base is threadedly attached to the implant element by way of the internal threaded bore so as to be disposed in a transmucosal abutment connection. After this attachment of the support base there is a further two to three week period to allow for healing of the tissue and integration of the support base with adjacent tissue, whereafter the prosthetic device is connected to the support base. It will be understood that the support base has an attachment for the mounting of the prosthetic device.

The existing procedures thus require significant time for completion, with the attendant discomfort and cost to the patient.

In orthopaedic surgery, much of the reconstructive therapy is based on the anchorage of metal prostheses in bone utilizing a space-filling bone cement, such as polymethylmethacrylate. This has been shown, however, to lead to osteocyte death due to mechanical, thermal and chemical injury. Eventual rejection may occur even if the implant is stably anchored to bone as the tissues are irreversibly damaged during the preparation of the recipient site. Furthermore, if the implant is connected to the external environment or immediately placed in function, both the initial loading stress and the ingrowth of microorganisms from the external environment lead to poor long-term prognoses.

Modifications of the implant design are being used in major facial reconstructive surgery. Implant therapy provides a foundation upon which prosthetic maxillofacial parts may be secured in patients who have become debilitated due to cancer, birth defects or traumatic injury.

DISCLOSURE OF THE INVENTION

This invention seeks to simplify implant procedures, and reduce the expense associated with such procedures.

Further this invention seeks to provide an improved method of placing an implant in which osseointegration between the implant and the bone is promoted.

Still further this invention seeks to provide an osseointegration promoting implant composition.

Still further this invention seeks to provide a composition for use in injecting a bore of a bone prior to placement of an implant in the bore.

Still further this invention seeks to provide the use of a transforming growth factor β in the manufacture of an osseointegration promoting composition.

Still further this invention seeks to provide an implant assembly.

In accordance with one aspect of the invention there is provided in a method of placing arm implant in bone, in which a bore is formed in the bone and the implant is inserted into the bore, the improvement in which a liquid composition comprising a transforming growth factor β (TGF-β) in a liquid carrier is injected into said bore prior to insertion of the implant in the bore, said liquid composition being gelable at about 37° C., and said TGF-β being present in said liquid composition in a concentration effective in an interspace between an inner surface of said bore and an outer surface of said implant, to promote osseointegration at the interface between said inner surface and said outer surface.

In accordance with another aspect of the invention there is provided an osseointegration promoting implant composition comprising a transforming growth factor β (TGF-β) in a liquid carrier, said liquid carrier being gelable at about 37° C., said TGF-β being present in said liquid carrier in an amount effective to promote osseointegration at the interface between a bore in a bone for an implant, and an outer surface of the implant.

In accordance with yet another aspect of the invention there is provided a composition comprising a transforming growth factor β (TGF-β) in a liquid carrier for use in injecting a bore of a bone prior to placing an implant in the bore, said liquid composition being gelable at about. 37° C., and said TGF-β being present in said liquid composition in a concentration effective in an interspace between an inner surface of said bore and an outer surface of said implant, to promote osseointegration at the interface between said inner surface and said outer surface; said composition having a liquid state at a temperature other than normal body temperature.

In accordance with still another aspect of the invention there is provided use of a transforming growth factor β (TGF-β) in the manufacture of an osseointegration promoting composition for injection into a bore of a bone prior to insertion of an implant in the bore, the TGF-β being present in a liquid carrier gelable at about 37° C., and being present in the composition in a concentration effective in an interspace between an inner surface of the bore and an outer surface of the implant, to promote osseointegration at the interface between the inner surface and the outer surface.

In accordance with yet another aspect of the invention there is provided an implant assembly which comprises, in combination, the aforementioned composition and an implant component having a stem for insertion in a bore in a bone, and a support base for a prosthesis, integral with the stem, the support base being located at a terminal end of the stem and being adapted to anchor the prosthesis.

DESCRIPTION OF PREFERRED EMBODIMENTS a) Implant

The implant is fabricated from a material which is non-toxic and harmless to biological tissue.

Suitably the implant is of titanium, but the implant can also be fabricated with a core of another metal or plastic, and an outer shell of titanium.

The invention will be further described for the particular embodiment in which at least the outer portion of the implant is of titanium, either as part of an implant having a body of titanium or as an implant having an outer coating or shell of titanium and a non-exposed core of another metal other solid material, for example, plastic or ceramic.

In particular the type of material used for implantation is a compromise to meet many different properties of mechanical strength, machinability elasticity and chemical reactivity. Titanium is generally the metal of choice for osseointegration. Commercially pure titanium is a light and relatively non-corrosive material which has the following composition: titanium (Ti) 99.75%, iron 0.05%, oxygen 0.10%, nitrogen 0.03%, carbon 0.05% and hydrogen 0.012%. Within milliseconds after manufacturing, titanium, as most metals, is covered with an oxide layer ($TiO_2$) of 2 to 5 nm in thickness. This oxide layer increases over the years when implanted into the body, and there is an active but gradual transitional zone from bulk metal through the oxide layer to the organic side. The purity of an implant is important because small changes in composition might change its electrochemical properties. During production, no surface of the final implant is touched by anything other than titanium-coated instruments.

The surface of the implant may suitably have indentations such as may be produced by sputtering; conveniently these indentations are to a depth of 100 μm to enhance the depth of the interspace between the inner surface of the bore in which the implant is to be inserted, and the outer surface of the implant, for osseointegration at the interface of the implant and the bore.

The surface of the implant may also comprise other surface irregularities providing a non-smooth outer surface, for example, raised ridges or ribs which also assist in providing the desired interspace for osseointegration. The ridges or ribs suitably extend helically over a portion of the implant surface and facilitate insertion of the implant in the bore.

The interface between a titanium implant and bone can be thought of as a zone, not as a distinct border, where non-living and living tissues interact resulting in osseointegration. The interface zone is dynamic, constantly being remodeled, adapted to the different stresses to which it is subject. The zone extends from the metal surface of the implant through its oxide layer to the host osseous tissues.

There is described herein a particular implant assembly namely a dental implant assembly comprising: a) an implant member having an elongate intrabony stem portion and a transmucosal base portion, integral therewith, b) a tooth prosthesis, and c) a locking member for securing said tooth prosthesis to said implant member.

b) implantation

The implant and the surgically formed bore in the bone are dimensioned so that the implant fits tightly in the bore after the death phase of the bone tissue at the inner surface of the bore. The tight fit provides an interspace between the outer surface of the implant and the inner surface of the bore of 10 to 100 microns, preferably up to 50 microns.

Following insertion of a metal implant into bone, within fractions of a second the oxide layer is exposed to a variety of biomolecules from the blood. The eventual bond strengths between an implant and bone are related to the adsorption or desorption of these biomolecules. No matter how carefully the bone is prepared a necrotic border zone will inevitably appear around a surgically created bone defect. The width of the zone depends upon the fractional heat generated with surgery and the degree of perfusion. For repair to occur at an implant site there must be adequate numbers of cells, adequate nutrition of these cells and a proper stimulus for bone repair.

The wound at the implantation site undergoes a healing process which is arbitrarily divided into four phases. During the first phase blood and exudates contact the implant surface and form a blood clot. This contains cellular elements of blood and noncellular elements of the fibrin network. It is believed that the adsorption and desorption of proteins then occurs. After a few hours, polymorphonuclear leucocytes (PMN), monocytes and other host cells adhere to and influence the surface of the implant to start osteogenesis. This adsorption of proteins is critical for the initial adhesion of cells, and therefore the final bond strength of the bone-implant surface. The second phase occurs after 48 hours and begins with tissue organization. Fibroblasts begin to produce collagen, non-collagenous proteins and other substances in the extracellular matrix. Capillaries sprout and macrophages and polymorphonuclear leucocytes appear and begin to dissolve and replace the blood clot. One week after implant insertion entry into phase three occurs. The generation of specific cells and their tissues, such as osteoblasts, chondroblasts, osteoclasts, hemopoietic tissue and new bone tissue, become evident. A bridging callus, originating a few millimeters from the implant margin, forms at the periosteal and endosteal surfaces. This forms a woven callus in rabbits in two weeks, which extrapolates into six weeks for humans. Phase four then involves the generation of new bone and its remodeling. This starts with a period of lamellar compaction. The lattice structure of the callus formed during phase three is now filled with lamellar bone and it is postulated that this process is complete within 18 weeks in humans. The next step is interface remodeling. One millimeter of bone next to the interface undergoes necrosis no matter what surgical technique is used. This does provide some structural support during the initial healing, but is eventually replaced by cutting or filling cones emanating from the endosteal surface at 18 weeks. The final step is maturation which occurs by about 54 weeks following implant insertion. The maturation and long-term maintenance of the rigid osseous fixation involves continual remodeling of the interface and its supporting bone.

c) Bone

The oxide surface of osseointegrated titanium implants is covered by a very thin layer of ground substance composed of proteoglycans and glucosaminoglycans attached to a backbone of hyaluronic acid. This layer is thought to be particularly important as proteoglycans form the biological glue responsible for adhesion between cells, fibrils and other structures.

Collagen filaments from the surrounding bone are usually arranged as a three dimensional lattice surrounding the implant at a distance from 200 Å to 1 μm. Gradually the fine filamentous network is replaced by bundles of collagenous fibers and fibrils, which are continuous with those of the surrounding bone. Processes from osteocytes also approach the titanium oxide surface, although they are always separated by a layer of ground substance at least 200 Å thick. Calcium deposits can be observed very close to the surface of the implant, lacking distinct demarcation from it.

Next to the ground substance is a layer of a collagenous matrix. There are three main groups of collagen structure at the interface. Type I collagen fibrils were regularly arranged and approached the oxide surface coming no closer than 500 Å. It is believed that a greater amount of Type I collagen fibrils is associated with successful osseointegration.

More recently, the concept of the ground substance layer has come into question. In an in vitro study, using an osteoblast culture method, it has been reported that an amorphous layer was found to exist next to the surface of titanium. Techniques have now been developed which allow for evaluation of the interface between a commercially pure titanium implant and bone. With the advent of the fracture technique and electropolishing, thin sections may be obtained to provide ultrastructural evaluation of the interface tissues.

d) Composition

The aforementioned description under items b) and c) makes it evident that a number of complex reactions occur between the surface of the implant and the bone tissue.

The introduction of the composition of TGF-β in a gelable liquid carrier into the bore of the bone prior to insertion of the implant is surprisingly found to be effective in speeding up the placement of the implant.

When the bore for the implant is formed in the bone, for example by drilling, the bore is rapidly filled with blood prior to placement of the implant, blood is typically sucked out of the bore prior to insertion of the implant, but blood will continue to enter the bore and blood is normally displaced when the implant is inserted in the bore. Prior attempts at speeding up the placement of the implant have been directed to coating the implant with a suitable coating material and the concept of attempting to insert a composition into the blood filled hole was not even considered, being, on the face of it, impractical.

These prior attempts have involved forming a coating of a gel, typically at room temperature, on the surface of the implant device, whereafter the gel coating is freeze dried on the device, and the device with the freeze dried coating is subjected to sterilization procedures. These prior compositions and the freeze dried coatings which they form are quite different from the liquid compositions of this invention; the prior compositions being essentially non-pourable gels at the point of use, applied in gel form to the implant device and being freeze dried to a solid coating which can be subjected to sterilization techniques. In contrast, the compositions of the invention are liquid at the point of use, but gelable at 37° C., and not intended to be freeze dried.

In particular the compositions of the invention are liquid at the point of use. In some cases, depending on the characteristics of the liquid carrier, it is necessary to cool the composition to a low temperature at which the composition is liquid, whereafter the liquid gels when exposed to body temperature, about 37° C., when injected in the liquid state into the bore, prior to insertion of the implant.

It will be understood that the composition of the invention need not necessarily be liquid at room temperature. The composition should, however, suitably have a liquid state at a temperature other than normal body temperature, either below or above normal body temperature, and a gel state at body temperature.

It will be understood that the composition may gel at a temperature above or below 37° C., provided that it will form a gel when exposed to the bore of the bone, at body temperature. Thus, for example, the composition may be a gel at normal ambient or room temperature of about 20° C., may have a liquid state below 10° C., and on injection in such liquid state at a temperature below 10° C. into the bore, will rapidly gel as the temperature of the composition rises to the temperature of the surroundings, i.e., body temperature.

Thus "gelable at about 37° C." means that the composition in a liquid state will gel when exposed to an environment having a temperature of about 37° C.; the gelling may in fact be completed at a temperature above or below 37° C.

In the liquid state the composition is suitably a readily flowable, pourable liquid having a consistency or viscosity comparable with that of water, such that it can be readily injected and, indeed will readily flow along small diameter passages. In the gel state, the composition is essentially non-pourable and not readily flowable, and may have a consistency or viscosity comparable with that of petroleum jelly.

Surprisingly the composition of the invention, when introduced directly into the bore is found not only to enhance the placement of the implant by significantly reducing the time for osseointegration, but also to promote haemostatis.

The transforming growth factor β (TGF-β) should be present in the composition in a concentration effective to promote osseointegration at the interface between the inner surface of the bore in the bone, and the outer surface of the implant, within the narrow interspace between these two surfaces.

In general the interspace will have a width of 10 to 100 μm, preferably up to 50 μm, and the TGF-β will be present in the composition in a concentration of 0.5 to 20 μg/ml, preferably 5 to 15 μg/ml.

The carrier is a liquid which has a gel state at about 37° C., and will thus gel at the physiological temperature in the bore of the bone.

This gelling of the liquid composition in the bore serves to prevent settling of TGF-β in the bore, and ensures that the TGF-β is available throughout the interface in which osseointegration is required. Additionally the gel provides slow and sustained release of the TGF-β.

Suitable liquid carriers which gel include collagen and polymers of the Pluronic (trademark) series which are polyoxyalkylene block copolymers having terminal hydroxyl groups, more especially α-hydro-ω-hydroxypoly (oxyethylene) poly(oxypropylene) poly(oxyethylene) block copolymers having a molecular weight of at least 1,000 and typically 1,000 to 16,000, in which the polyoxypropylene segments are hydrophobic and the polyoxyethylene segments are hydrophilic.

In general the block copolymers may be represented by the formula:

where segment b comprises at least 15%, by weight, and segments a+c comprise 20 to 85%, by weight.

This latter class of block copolymers display inverse solubility characteristics and are non-toxic or of low toxicity. These block copolymers, when dissolved in water or aqueous media form compositions which gel as their temperature is raised, but revert to liquid solutions as their temperature is lowered. In other words, the gels are reversible; cooling the gel converts the gel state to the liquid phase,.increasing the temperature converts the liquid phase to the gel state. The gel can be cooled down and warmed up repeatedly with no change in properties other than conversion between the gel and liquid states.

These block copolymers when dissolved in water or aqueous media, typically in a concentration of 15 to 60%, by weight, depending on the molecular weight, form liquid carriers suitable for the composition of the invention.

An especially preferred block copolymer is Pluronic polyol F-127 which chemically is an ether alcohol. It is composed of 70% ethylene oxide to 30% propylene oxide (by weight) and is available commercially as a solid white flake. These characteristics are reflected in its name (F(flake) -12 (molecular weight about 12,500)-7(70% ethylene oxide).

Pluronic F-127 has a melting point of 56° C. and a specific gravity of 1.04 (77° C.) and viscosity of 3100 Cps (Brookfield, solid at 77° C.) It is soluble in water, although it dissolves very slowly, and it gels in water with concentrations between 15 and 30%, preferably about 25%, by weight. As the concentration of F-127 increases the gel becomes harder. It is more soluble in cold than hot water.

Pluronic polyol F-127 is one of a series of high molecular weight block copolymers of ethylene and propylene oxide. Its synthesis occurs, under conditions of elevated temperature and pressure, and in the presence of basic catalysts, for example, NaOH or KOH, when propylene oxide is slowly added to the two hydroxyl groups of a propylene glycol initiator to form a 4000 molecular weight polyoxypropylene glycol. This is referred to as the hydrophobe. To this hydrophobe, ethylene oxide is slowly added until a final molecular weight product of about 12,500 is attained. This reaction is neutralized with phosphoric acid at pH 7.

In general terms, a hydrophobe of desired molecular weight is created by the controlled addition of propylene oxide to propylene glycol. Ethylene oxide is then added to sandwich the hydrophobe between its hydrophillic groups. Controlled by length, ethylene oxide may represent, by weight, between 15% and 85% of the final molecule.

High molecular weight formulations of the Pluronic gets are non-toxic. As the molecular weight of hydrophobe (polyoxypropylene) or the proportion of ethylene oxide (% polyoxyethylene) increases the toxicity decreases from very slightly toxic to nontoxic. LD50 determinations (acute and chronic doses included in food in rodents and dogs) and three generation reproduction study have determined no ill effects for the Pluronic block copolymers.

Transforming growth factor $\beta_1$ has a number of distinct members within its family, for example, TGF-$\beta_1$ and TGF-$\beta_2$. In the present invention TGF-$\beta_1$ is especially preferred, however, other members of the TGF-$\beta$ family which promote osseointegration may be employed as well as mixtures of different members of the family.

The composition may suitably be provided in combination with instructions for use of the composition in placement of an implant in a bore in a bone, such instructions including directions for injection of the liquid composition into the bore, prior to insertion of the implant in the bore. The instructions may suitably appear on packaging associated with the composition, for example, on the labels of a container for the composition or on inserts or leaflets contained in outer packaging housing a container of the composition.

The composition has, in particular, a liquid form suitable for or adapted to be injected into the bore, prior to insertion of an implant in the bore.

e) Dental Implant Assembly

There is disclosed herein a novel dental implant assembly which has three basic components, as compared with the five basic components of the prior dental implant assemblies, such as those of the Branemark System (Trade Mark of Nobelpharma).

The composition of the invention is not restricted to use with the novel assembly, however, the assembly is especially suitable for use in conjunction with the liquid composition of the invention and provides a less complex structural assembly which can be mounted in a much shorter period of time.

The assembly includes an implant member, a tooth prosthesis and a locking member for securing the tooth prosthesis to the implant member.

The implant member has an elongate intrabony stem portion and a transmucosal base portion, integral with the stem portion.

In particular the tooth prosthesis has a body portion and a spigot projecting from the body portion, and the transmucosal base portion has a cavity for matingly receiving the spigot to mount the tooth prosthesis on the transmucosal base portion.

A prosthesis bore extends through the body portion of the tooth prosthesis and communicates with a bore which extends through the spigot.

The spigot and the receiving cavity of the transmucosal base portion are suitably shaped complementary, to permit axial entry of the spigot into the receiving cavity, while preventing relative rotation of the spigot and receiving cavity.

A threaded bore in the elongate, intrabony stem portion of the implant member communicates with the prosthesis bore and the locking member has an elongate threaded stem which can be fed through the prosthesis bore for threaded engagement with the threaded bore in the intrabony stem portion.

In an especially preferred embodiment the intrabony stem portion includes a plurality of flow passages, each of which has an inlet end communicating with the threaded bore of the intrabony stem portion, and an outlet end which communicates with an outer surface of the intrabony stem portion.

In an especially preferred embodiment the intrabony stem portion has a plurality of flutes defined in its outer surface, which -flutes are substantially C-shaped, and define channels extending axially of the outer surface of the intrabony stem portion, from an inner end of such stem portion towards the transmucosal base portion. Suitably the flutes extend for two-thirds of the length of the intrabony stem portion, and the outlet ends of the flow passages communicate with the flutes.

The flow passages permit introduction of additional quantities of the liquid composition of the invention to the interspace between the bore of the bone and the intrabony stem portion, after initial mounting.

Preferably the surface of the intrabony stem portion is sputtered to provide a plurality of dimple-like indentations for housing the liquid composition in the interspace. These indentations will typically have a depth of up to 100 μm.

MODES FOR CARRYING OUT THE INVENTION

Figure 1:
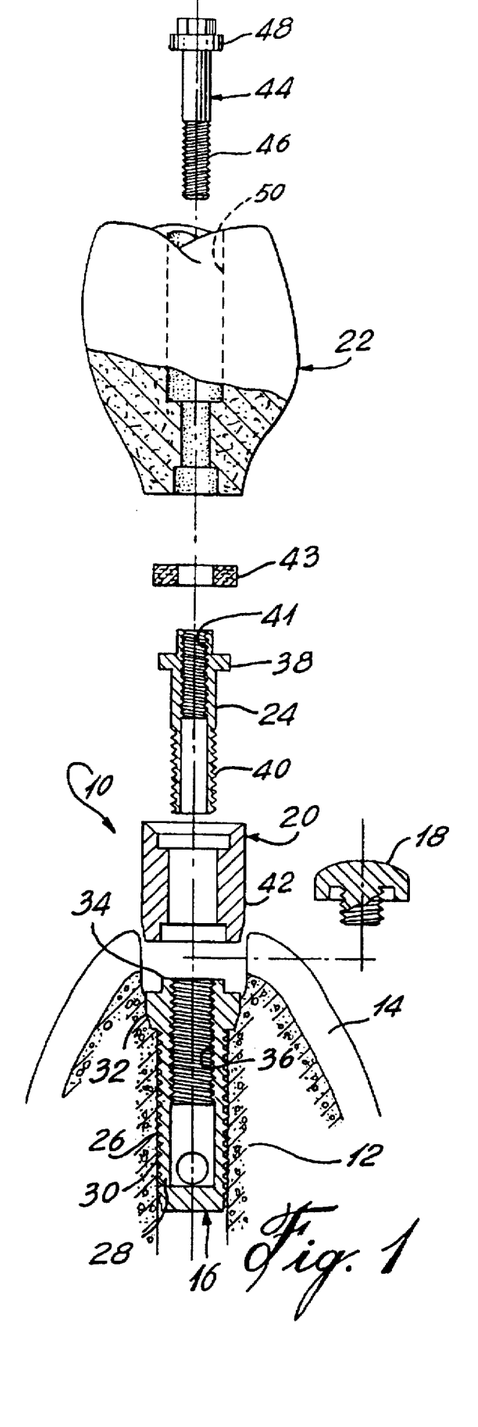
FIG. 1 is an exploded view of a Prior Art dental implant assembly.

With further reference to FIG. 1, there is shown an exploded view of a prior art dental implant assembly 10 of the type employed in the Branemark System (Trade Mark of Nobelpharma).

Dental implant assembly 10 is to be mounted in bone 12 having gum tissue 14 thereabout.

Dental implant assembly 10 includes a screw-like implant member 16, a temporary cover 18, a support base or abutment assembly 20 and a tooth prosthesis 22.

A bore 26 is formed in bone 12 for receiving the implant member 16.

The implant member 16 has an elongate stem 28 having a threaded surface 30, a non-threaded collar 32 and a terminal hexagonal nut 34. An internal threaded bore 36 extends from hexagonal nut 34 inwardly of implant member 16.

The abutment assembly 20 includes a sleeve 42 and a separate abutment screw 24. Abutment screw 24 includes a threaded stem 40 and a head 38. Stem 40 has an internal threaded bore 41. An annular collar 43 engages head 38.

A bore 50 extends through tooth prosthesis 22, allowing passage of a mounting screw 44. Mounting screw 44 has a threaded stem 46 and a head 48.

In the attachment of the dental implant assembly 10, incisions are made in gum tissue 14 over bone 12 and a flap of gum tissue 14 is folded back to provide access to bone 12.

Bore 26 is formed in the exposed bone 12 by drilling.

Stem 28 of implant member 16 is inserted in bore 26 and is threaded into the bore 26 by way of threaded surface 30, to securely locate implant member 16 in the bone 12. In this regard implant member 16 is screwed into the bore 26 of bone 12 until the non-threaded collar 32 and hexagonal nut 34 are below the surface of the surrounding gum tissue 14. Typically threaded surface 30 will be self-tapping.

The temporary cover 18 is applied to hexagonal nut 34 to temporarily close the bore 36 in implant member 16 and the previously formed flap of gum tissue is thereafter restored to position over the temporary cover 18 and is sutured in place to provide a continuous gum tissue surface.

A period of three to six months is required to permit healing of the bone tissue and gum tissue around the implant member 16 and initial osseointegration of the implant member 16 with the surrounding bone.

After the three to six month period a small hole is punched in the gum tissue 14 over the temporary cover 18, the temporary cover 18 is removed and abutment assembly 20 is mounted on implant member 16.

The mounting of abutment assembly 20 involves mounting sleeve 42 over hexagonal nut 34 with which it mates so that the sleeve 42 rests on collar 32. Sleeve 42 is located below the surface of gum tissue 14, and is locked in place by the abutment screw 24 by engagement of the threaded stem 40 with the internal threaded bore 36 of implant member 16.

The sleeve 42 of the abutment assembly 20 thus forms a transmucosal element adjacent the exposed gum tissue 14.

A further period, typically about two weeks is now required for healing of the gum tissue in the vicinity of the transmucosal element (sleeve 42). During this period a further temporary cover (not shown) may be secured to the head 38 of abutment screw 24 to close bore 41.

Subsequently, collar 43 is applied about head 38 and the tooth prosthesis 22 is placed over head 38 of abutment screw 24 and is seated on an upper face of collar 43. Mounting screw 44 is fed through bore 50 of tooth prosthesis 22 and threaded stem 46 is screwed into engagement with the threaded bore 41 in abutment screw 24, to securely fix tooth prosthesis 22 to abutment assembly 20.

With further reference to FIGS. 2 to 5 there is illustrated a dental implant assembly 100 of the invention.

Figure 2:
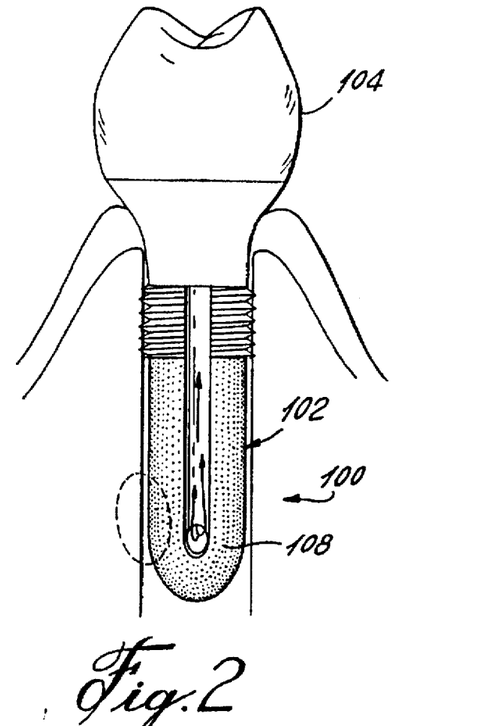
FIG. 2 is a schematic elevation of a mounted dental implant assembly of the invention.
Figures 3, 5:
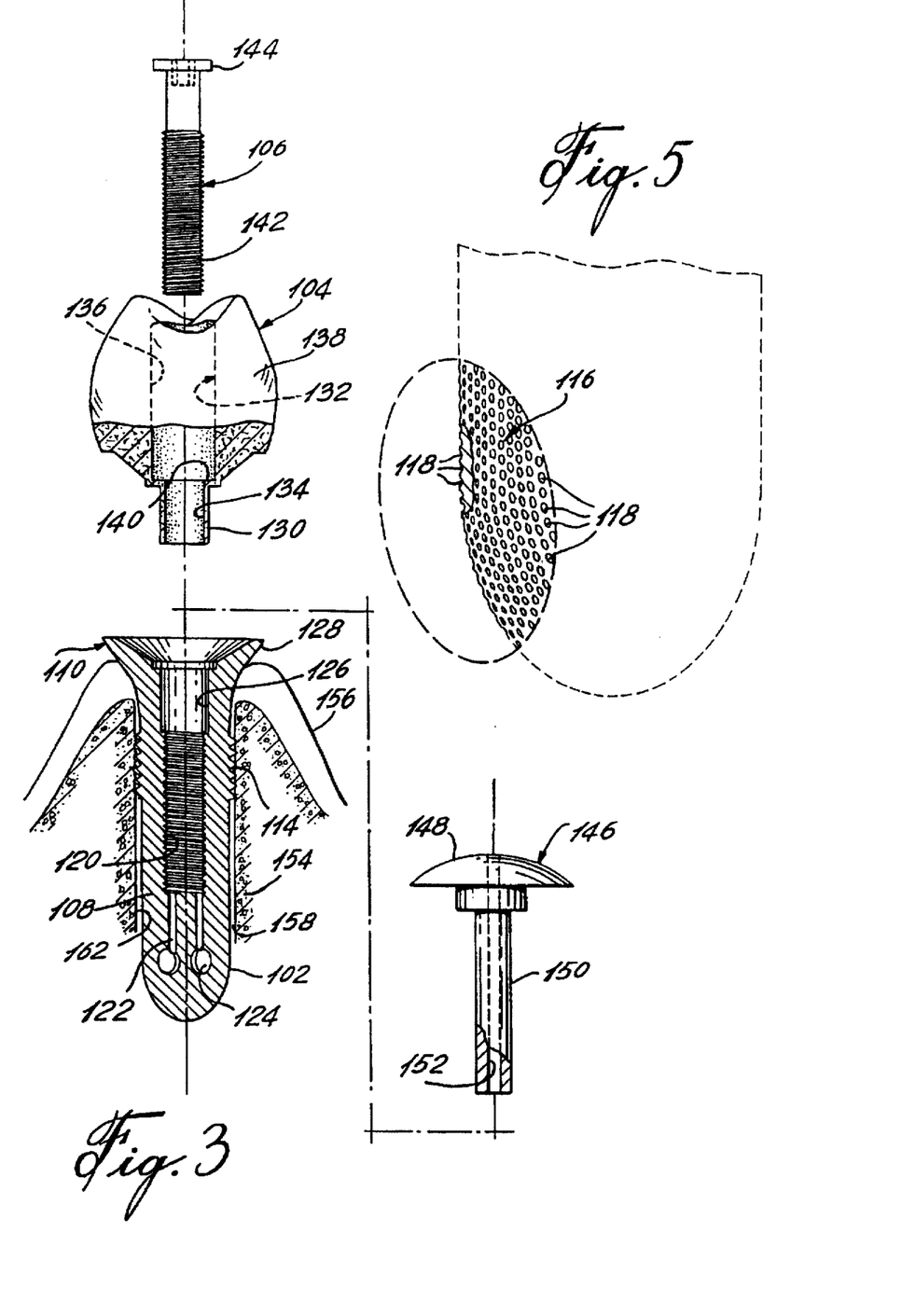
FIG. 3 is an exploded view of the dental implant assembly of FIG. 2.
FIG. 5 shows a detail of the sputtered surface of the stem of the implant member of the assembly of FIG. 2.

Dental implant assembly 100 includes an implant member 102, a tooth prosthesis 104 and a mounting screw 106.

Implant member 102 has an intrabony stem 108 and a transmucosal base 110 integral with stem 108.

Figure 4:
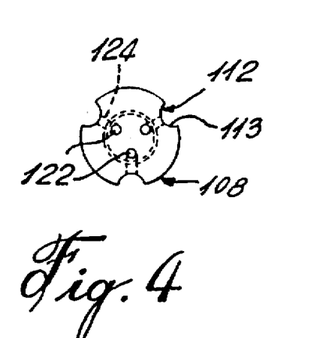
FIG. 4 is a cross-section of a lower end of the stem of the implant member of the assembly of FIG. 2.

Stem 108 has a plurality, typically 3, of flutes 112 extending axially along an outer surface and terminating adjacent a threaded portion 114 of stem 108 (FIG. 4). Flutes 112 define flow channels 113 along the surface 116 of stem 108 and are suitably spaced symmetrically about outer surface 116.

Outer surface 116 is suitably sputtered (FIG. 5) providing a plurality of small indentations 118, typically having a depth of up to 100 microns.

Stem 108 has an internal threaded bore 120 in flow communication with a plurality, typically 3, of flow passages 122 which terminate in ports 124. Each port 124 opens into a flute 112 thereby providing a flow passage from the bore 120 through flow passages 122 and ports 124 to the channels 113.

Transmucosal base 110 has an ovular passage 126 therethrough which communicates with the internal threaded bore 120 of intrabony stem 108. Transmucosal base 110 has a flared upper end which reflects the normal anatomic contours of a tooth so as to provide for optimal aesthetics, function and hygiene.

Tooth prosthesis 104 has an ovular spigot 130 projecting from a tooth body 138.

A prosthesis bore 132 extends completely through tooth prosthesis 104 and includes a bore 134 in ovular spigot 130 which communicates with a bore 136 of larger diameter in body 138, a floor 140 being formed at the junction of bore 136 and bore 134.

Mounting screw 106 includes a threaded stem 142 and a head 144.

During installation a temporary cap 146 is employed in conjunction with the dental implant assembly 100; cap 146 has a head 148 a stem 150 and an injection passage 152 extending the length of stem 150 and having an opening into head 148.

The dental implant assembly 100 of the invention thus comprises three basic components, the implant member 102, the tooth prosthesis 104 and the mounting screw 106, and utilizes the temporary cap 146. In contrast the prior art dental implant assembly 10 of FIG. 1 has five basic components, the screw-like implant member 16, the two component abutment assembly 20 which includes the abutment screw 24 and the sleeve 42, the tooth prosthesis 22 and the mounting screw 44, and is employed in conjunction with temporary cover 18, and possibly a second temporary cover.

The assembly of the invention in addition to having less parts is less complex in design and permits the restorative dental work to be completed in a significantly shorter time.

In operation the gum tissue 156 over the site for the implant is first surgically cut to form a flap to expose the site, and a bore 154 is drilled into the bone 160. These steps are the same as for the prior art system described with reference to FIG. 1. Blood is syphoned from bore 154 which has an inner wall 162. The liquid composition of the invention is injected into the bore 154 whereafter the implant member 102 is inserted into the bore, providing an interspace 158 between bore wall 162 and outer surface 116, which interspace 158 is occupied by the liquid composition. The initial placement of the implant member 102 allows for a simple press-fit placement of the implant since typically the lower two-thirds of the intrabony stem 108 is not threaded but has the flutes 112 therein. Thereafter the threaded portion 114 of stem 108, which threaded portion 114 is typically of a self-tapping thread, allows for accuracy in the final seating of the implant member 102 in the bore 154. At this final seating the transmucosal base 110 extends to the surface of the surrounding gum tissue 156.

At this stage the liquid composition of the invention is held within the interspace 158 between the bore 154 and the intrabony stem 108. The channels 113 facilitate delivery of the liquid composition throughout the interspace 158 and the indentations 118 of the sputtered surface 116 provide multiple sites for holding the liquid composition in the interspace 158, throughout the length of bore 154.

The liquid composition promotes osseointegration between the surface 116 of intrabony stem 108 which is typically a biologically flawless titanium surface, and the wall 162 of bore 154. The threaded portion 114 is also found to provide a greater retention of bony height and increased long term success.

At this stage temporary cap 146 is placed on transmucosal base 110 so that head 148 provides a top cover and stem 150 extends axially of internal threaded bore 120.

Periodically, if desired, fresh liquid composition can be introduced to the interspace 158 by injection through injection passage 152 of stem 150 of temporary cap 146, liquid composition thereby flowing from injection passage 152 into flow passages 122 through ports 124 and into the channels 113 from which the composition is delivered to the interspace 158.

Osseointegration between the bone wall 162 of bore 154 and the surface 116 of intrabony stem 108, and healing between the gum tissue 156 and transmucosal base 110 is complete in a period of not more than one month, typically about three weeks.

In the second and final stage of the installation the temporary cap 146 is removed, the tooth prosthesis 104 is placed by inserting ovular spigot 130 into ovular passage 126 whereby ovular spigot 130 is matingly received by ovular passage 126. The mating ovular shape of the spigot 130 and passage 126 permits axial movement of the spigot 130 in the passage 126 but prohibits relative rotary movement thereby providing long term strength and stability in the final prosthesis.

Finally, tooth prosthesis 104 is fixed in place by means of mounting screw 106. Threaded stem 142 is fed through prosthesis bore 132 to threadedly engage internal threaded bore 120 within intrabony stem 108 and is threaded into engagement until head 144 engages floor 140.

The dental implant assembly of the invention permits mounting of a dental prosthesis in a much shorter period of time with a shortening of the period of discomfort to the patient, employing an assembly of a smaller number of parts, with an overall reduction in the total expense of installation.

EXAMPLES

Example 1

A liquid carrier based on an aqueous solution of Pluronic F-127 was prepared by a "cold" technique. To a 250 ml beaker containing 75 g of cold (5°–10° C.) water, 25 g (25% solution) of the F-127 stock is slowly added, over a period of 5–10 min. The beaker contains a magnetic stirring bar which provides gentle mixing. Too rapid addition of the F-127 will result in the formation of a ball which will then require many hours to go into solution. Mixing the solution can take up to 4 hours with gentle agitation or overnight if left in a quiescent state. The carrier is prepared and stored at 4° C. Soft gels of F-127 are formed at concentrations in water of 18 to 25% by weight. Higher concentrations (30% or >) require temperatures as low as 0° C. The gel is reversible, in that it can be warmed or cooled a number of times without altering its properties. An important consideration for in vivo use is that F-127 in this concentration range (18–25%) gels rapidly within the range of 15°–80° C.

In rat studies on bone healing, concentrations of TGF-$\beta_1$ (in 5 mM HCl, stored at 4° C.) between 0.5 and 16 µl are added to 100 µl total of carrier gel (25% F-127) at 4° C. These aliquots are prepared and kept on ice the morning of the experiment. All pipette tips, Ependorf tubes, are kept on ice until the TGF-$\beta_1$ is applied to the wound site. In applying the compositions to the wound area, haste is necessary as the composition gels within seconds upon removal from the ice. Problems experienced in applying the liquid compositions to the wound site, however, can be remedied by returning the composition to the ice.

Example 2

Titanium implants were cleaned in an ultrasonicator cleaner for 10 minutes while placed in a glass container of hydrated n-butanol and then in 99% ethanol for another 10 min. The implants were finally placed in a titanium Container and steam autoclaved for sterilization.

Male Sprague-Dawley rats weighing 300 grams were anaesthetized with sodium pentobarbital and placed in a laminar flow hood to prevent contamination and minimize the risk of infection. The hind leg was immobilized, prepared with a proviodine solution, shaved and a longitudinal incision made along the anterior aspect of the tibia. The incision was made through the skin, the underlying muscle bellies were carefully separated to expose the periosteum, which was incised longitudinally and then relocated to expose the anterior aspect of the tibia. The implant site was selected and drilled to form a bore under a No. 1 round bur at 1000 revolutions per minute. A titanium hand held tap was used to tap the recipient bore site. TGF-$\beta$ in a liquid Pluronic carrier was injected into the bore of the bone, and finally, the titanium implant (2.0 mm in length and 1.25 mm in diameter) was screwed in the tibia. An attempt was made to engage both cortices of bone when placing the implant and all stages of implant placement are performed utilizing copious saline irrigation. The periosteum was then reapproximated, the muscle bellies closed with 4-0 plain catgut sutures, and the skin sutured with 4-0 Dexon (Trade Mark for a polyglycolic acid) sutures.

At the resolution of the light microscope the desired contact was observed between the surface of the implant and the bone, after 3 weeks. When the procedure was repeated without the use of the TGF-$\beta$, the desired contact was not observed until after 6 weeks.

I claim:

1. An osseointegration promoting implant composition having a liquid form adapted to be injected in a bore in a bone prior to insertion of an implant in the bore, said liquid form readily flowing along an interspace between said bore and said implant of 10 to 100 microns width, said composition consisting essentially of a transforming growth factor β (TGF-β) in a liquid carrier, said liquid carrier being gelable at about 37° C., said TGF-β being present in said liquid carrier in an amount effective to promote osseointegration at the interface between the bore and the bone for the implant, and an outer surface of the implant; said composition having a liquid state at a temperature other than normal body temperature, said liquid carrier being effective in gel form at about 37° C. to prevent settling of the TGF-β in the composition and provide slow and sustained release of the TGF-β, at the interface between the bore in the bone for the implant, and the outer surface of the implant, said liquid carrier consisting essentially of an inversely soluble polyoxyalkylene block copolymer having a molecular weight of at least 1000 and bearing terminal hydroxyl groups, in an aqueous medium.

2. A composition according to claim 1, wherein said TGF-β is TGF-$\beta_1$.

3. A composition according to claim 1, wherein said polyoxyalkylene block copolymer has a molecular weight of 1000 to 16,000, said composition reversibly interchanging between gel and liquid states, dependent on temperature.

4. A composition according to claim 2, wherein said TGF-$\beta_1$ is present in a concentration of 5 to 15 µg/ml.

5. A composition according to claim 1, wherein said liquid carrier is a liquid at a temperature below 10° C. and said polyoxyalkylene block copolymer has a molecular weight of about 12,500, and is in said aqueous medium, in a concentration of about 15 to 30%, by weight, said block copolymer being composed of about 70% ethylene oxide and 30% propylene oxide, by weight, said composition reversibly interchanging between gel and liquid states, dependent on temperature.

6. A composition consisting essentially of a transforming growth factor β (TGF-β) in a liquid carrier having a liquid form adapted to be injected in a bore of a bone prior to placing an implant in the bore, said liquid form being a readily flowable, pourable liquid having a viscosity comparable with that of water such that it can be readily injected and will flow along an interspace between the bore and the implant of 10 to 100 microns width, said gel being essentially non-pourable having a viscosity comparable with that of petroleum jelly, said liquid composition being gelable at about 37° C., and said TGF-β being present in said liquid composition in a concentration effective in the interspace between an inner surface of said bore and an outer surface of said implant, to promote osseointegration at the interface between said inner surface and said outer surface; said composition having a liquid state at a temperature other than normal body temperature, said liquid carrier consisting essentially of an inversely soluble polyoxyalkylene block copolymer having a molecular weight of at least 1000 and bearing terminal hydroxyl groups, in an aqueous medium.

7. A composition according to claim 6, wherein said liquid carrier is a liquid at a temperature below 10° C. and said polyoxyalkylene block copolymer has a molecular weight of about 12,500, and is in said aqueous medium, in a concentration of about 15 to 30%, by weight, said block copolymer being composed of about 70% ethylene oxide and 30% propylene oxide, by weight, said composition reversibly interchanging between gel and liquid states, dependent on temperature.

8. A composition according to claim 6, wherein said TGF-β is TGF-β-1 present in a concentration of 5 to 15 µg/ml.

9. A composition according to claim 7, wherein said TGF-β is TGF-β-1 present in a concentration of 5 to 15 µg/ml.

10. A composition according to claim 1, wherein said polyoxyalkylene block copolymer is represented by $$HO(CH_2CH_2O)_a-(CH(CH_3)CH_2OH)_b(CH_2CH_2O)_cH$$

where segment b comprises at least 15%, by weight, and segments a+c comprise 20 to 85%, by weight.

11. A composition according to claim 6, wherein said polyoxyalkylene block copolymer is represented by $$HO(CH_2CH_2O)_a-(CH(CH_3)CH_2OH)_b(CH_2CH_2O)_cH$$

where segment b comprises at least 15%, by weight, and segments a+c comprise 20 to 85%, by weight.

* * * * *

UNITED STATES PATENT AND TRADEMARK OFFICE
CERTIFICATE OF CORRECTION

PATENT NO. : 5,702,695
DATED : December 30, 1997
INVENTOR(S) : CAMERON MALCOLM LANG CLOKIE It is certified that error appears in the above-identified patent and that said Letters Patent is hereby corrected as shown below:

In Column 6, line 60,
"$HO(CH_2CH_2O)_a-(CH(CH_3)CH_2OH)_b(CH_2CH_2O)_cH$"
should read as follows:
--$HO(CH_2CH_2O)_a-(CH(CH_3)CH_2O)_b-(CH_2CH_2O)_cH$--.

In Column 14, claim 11, line 36,
"$HO(CH_2CH_2O)_a-(CH(CH_3)CH_2OH)_b(CH_2CH_2O)_cH$"
should read as follows:
--$HO(CH_2CH_2O)_a-(CH(CH_3)CH_2O)_b-(CH_2CH_2O)_cH$--.

Signed and Sealed this

First Day of May, 2001

Attest:

NICHOLAS P. GODICI

Attesting Officer       Acting Director of the United States Patent and Trademark Office